(12) United States Patent
Chen

(10) Patent No.: US 10,602,780 B2
(45) Date of Patent: Mar. 31, 2020

(54) ELECTRONIC CIGARETTE

(71) Applicant: SHENZHEN IVPS TECHNOLOGY CO., LTD., Shenzhen, Guangdong Province (CN)

(72) Inventor: Wen Chen, Shenzhen (CN)

(73) Assignee: Shenzhen IVPS Technology Co. Ltd. (CN)

(*) Notice: Subject to any disclaimer, the term of this patent is extended or adjusted under 35 U.S.C. 154(b) by 219 days.

(21) Appl. No.: 15/917,603

(22) Filed: Mar. 10, 2018

(65) Prior Publication Data

US 2019/0053542 A1 Feb. 21, 2019

(30) Foreign Application Priority Data

Jan. 10, 2017 (CN) .................... 2017 2 0027030 U

(51) Int. Cl.
```
A24F 13/00      (2006.01)
A24F 47/00      (2020.01)
A61M 11/04      (2006.01)
A61M 15/06      (2006.01)
H05B 3/44       (2006.01)
A24F 1/32       (2006.01)
B67D 7/02       (2010.01)
```
(52) U.S. Cl.
CPC ......... *A24F 47/008* (2013.01); *A61M 11/042* (2014.02); *A61M 15/06* (2013.01); *H05B 3/44* (2013.01); *A24F 1/32* (2013.01); *A61M 2205/3653* (2013.01); *A61M 2205/8206* (2013.01); *B67D 7/0288* (2013.01); *H05B 2203/021* (2013.01)

(58) Field of Classification Search
CPC ...................................... A24F 47/00
USPC ................................... 131/328-329
See application file for complete search history.

(56) References Cited

U.S. PATENT DOCUMENTS

| | | | | |
|---|---|---|---|---|
| 2015/0034104 A1* | 2/2015 | Zhou | ..................... | A24F 47/008 131/329 |
| 2015/0272217 A1* | 10/2015 | Chen | ..................... | A24F 47/008 131/329 |

FOREIGN PATENT DOCUMENTS

| | | |
|---|---|---|
| CN | 204888738 U | 12/2015 |
| CN | 107581662 A | 1/2018 |
| CN | 107616553 A | 1/2018 |

\* cited by examiner

*Primary Examiner* — Phuong K Dinh
(74) *Attorney, Agent, or Firm* — IP-PAL Patent US

(57) ABSTRACT

The disclosure provides an electronic cigarette, wherein the electronic cigarette comprises an upper-cover assembly and a lower-cover assembly. The upper-cover assembly and the lower-cover assembly are cooperated to together form an oil-storing chamber. The lower-cover assembly comprises a connecting element, a bottom cover and a sealing element detachably connected to the bottom cover. One end of the connecting element is connected with the bottom cover, and the other end of the connecting element is connected with the upper-cover assembly. The bottom cover defines an oil-refilling hole. The connecting element defines a through hole communicating with both the oil-refilling hole and the oil-storing chamber. When the sealing element is connected with the bottom cover, the sealing element extends through the oil-refilling hole and is accommodated in the through hole. The electronic cigarette of the present disclosure has a simplified structure and is able to be refilled with oil conveniently, avoiding oil-leakage.

10 Claims, 4 Drawing Sheets

ELECTRONIC CIGARETTE

TECHNICAL FIELD

The present disclosure relates to technical field of electronic cigarette, especially to an electronic cigarette.

BACKGROUND

As an alternatives to cigarettes or as a way of quitting smoking, electronic cigarettes could simulate using effect of normal cigarettes and removes harmful composition such as tars, suspended particles in normal cigarettes, being sought after by people. At present, the electronic cigarettes in the market commonly adopt top oil-refilling structure. When refill with oil, the whole upper assembly or the heating assembly needs to be disassembled and the operation is complex, affecting user experience. There are other electronic cigarettes adopting bottom oil-refilling structure. However, several elements of electronic cigarette need to be disassembled. And it also has the disadvantages of oil-leakage and inconvenience of operation.

SUMMARY

The aims of the present disclosure is to provide an electronic cigarette so as to have a simplified structure, conveniently refill oil and avoid oil-leakage.

To realize the above aims, the present disclosure provide an electronic cigarette. The electronic cigarette comprises an upper-cover assembly and a lower-cover assembly interconnected with the upper-cover assembly. The upper-cover assembly and the lower-cover assembly are cooperated to together form an oil-storing chamber. The lower-cover assembly comprises a connecting element, a bottom cover and a sealing element detachably connected to the bottom cover. One end of the connecting element is connected with the bottom cover, and the other end of the connecting element is connected with the upper-cover assembly. The bottom cover defines an oil-refilling hole and the connecting element defines a through hole communicating with both the oil-refilling hole and the oil-storing chamber. When the sealing element is connected with the bottom cover, the sealing element extends through the oil-refilling hole and is accommodated in the through hole.

Preferably, the electronic cigarette comprises a heating assembly having an atomizing chamber. The upper-cover assembly comprises a casing and a connecting tube set inside the casing. The connecting tube is connected with the heating assembly and communicates with the atomizing chamber.

Preferably, the bottom cover defines an air-inlet hole. One end of the heating assembly far away from the connecting tube is connected with the bottom cover and the atomizing chamber communicates with the air-inlet hole. The casing, the connecting tube, the heating assembly and the bottom cover are cooperated to together form the oil-storing chamber.

Preferably, the bottom cover partially located inside the casing. A mounting groove is defined in an end part of the bottom cover located inside the casing. The connecting element is partially accommodated in the mounting groove. A part of the connecting element exposed from the mounting groove abuts against an inner wall of the casing.

Preferably, the heating assembly further comprises an atomizing casing defining the atomizing chamber and a heating wire located in the atomizing chamber. The atomizing casing defines an oil permeation hole communicating with both the atomizing chamber and the oil-storing chamber.

Preferably, a quantity of the oil permeation hole is two. The heating assembly further comprises heating-wire cotton, and the heating-wire cotton is wound by the heating wire. Two ends of the heating-wire cotton extend through the two oil permeation holes respectively and locate inside the oil-storing chamber.

Preferably, the atomizing casing comprises a first casing and a second casing detachably interconnected with the first casing. The first casing and the second casing are provided with a female fastener and a male fastener respectively. When the first casing is connected with the second casing, a contacting part between the female fastener and the male fastener defines the two oil-leaking holes.

Preferably, the electronic cigarette further comprises a smoking mouthpiece detachably connected to the casing. The smoking mouthpiece comprises an air pipe. When the smoking mouthpiece is connected to the casing, the air pipe at least partially locates in the connecting tube and communicates with the connecting tube.

Preferably, the electronic cigarette further comprises two contacting pins. The bottom cover defines two openings communicating with the atomizing chamber. One end of each contacting pin extends through a respective opening and is connected with one end of the heating wire.

Preferably, the first casing is made of rubber.

In the technical solution of the present disclosure, one end of the connecting element is connected with the bottom cover, and the other end of the connecting element is connected with the upper-cover assembly. The bottom cover defines an oil-refilling hole, and the connecting element defines a through hole communicating with both the oil-refilling hole and the oil-storing chamber. When the sealing element is connected with the bottom cover, the sealing element extends through the oil-refilling hole and is accommodated in the through hole so that the electronic cigarette has a simplified structure and is able to be conveniently refilled with oil and avoid oil-leakage.

BRIEF DESCRIPTION OF THE DRAWINGS

For a better understanding of the embodiments of the present disclosure or the technical scheme in the prior art, accompanying drawings needed in the description of the embodiments or the prior art are simply illustrated below. Obviously, the accompanying drawings described below are some embodiments of the present disclosure. For the ordinary skill in the field, other accompanying drawings may be obtained according to the structure shown in these accompanying drawings without creative work.

DESCRIPTION OF THE REFERENCE NUMBER

Figure 1:
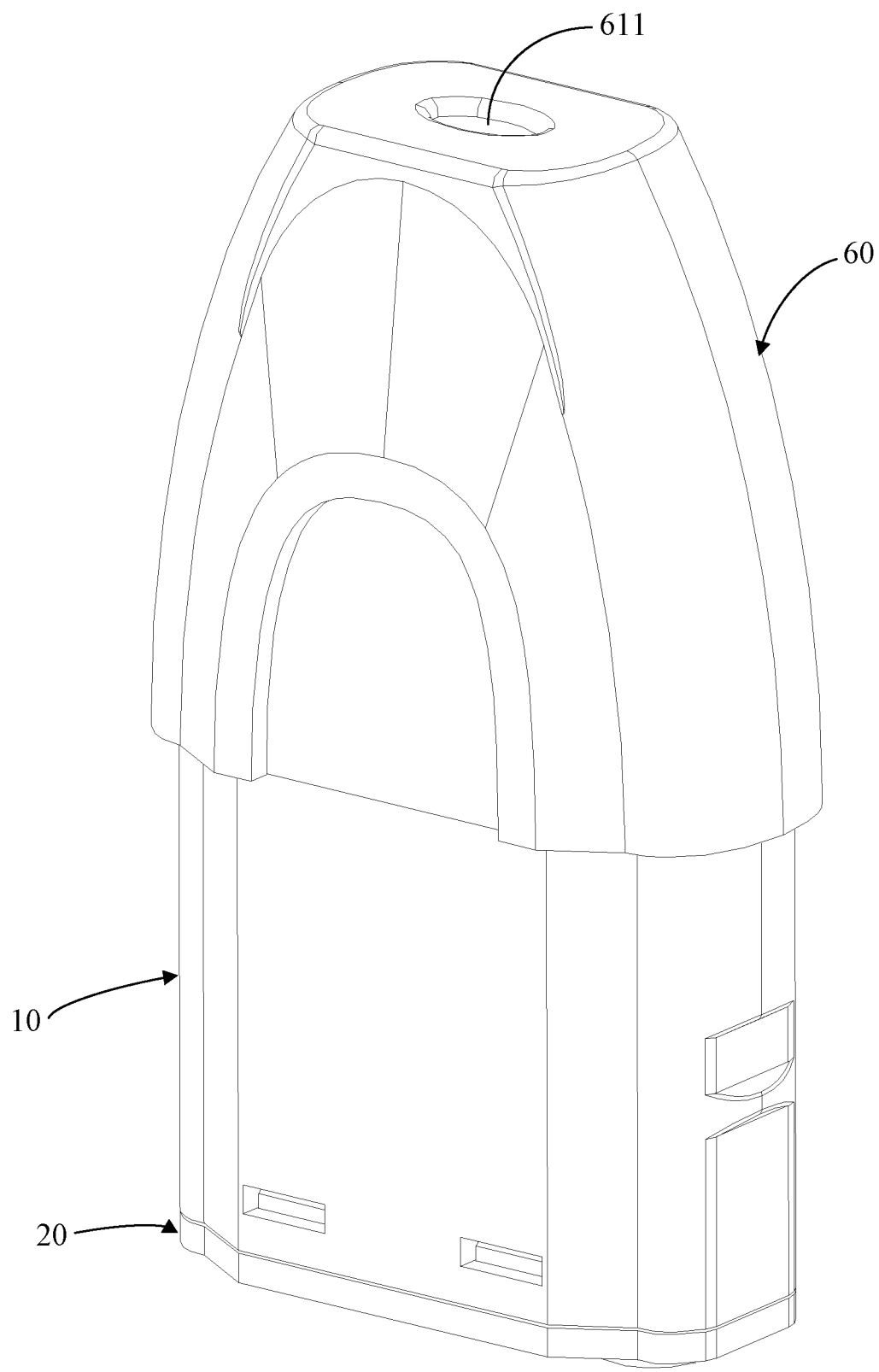
FIG. 1 is a three-dimensional view of the embodiment of the electronic cigarette in the present disclosure.

| Reference number | Part |
| --- | --- |
| 10 | upper-cover assembly |
| 11 | casing |
| 12 | connecting tube |
| 20 | lower-cover assembly |
| 21 | bottom cover |
| 211 | oil-refilling hole |
| 212 | air-inlet hole |
| 213 | mounting groove |
| 22 | sealing element |
| 23 | connecting element |
| 231 | through hole |
| 30 | oil-storing chamber |
| 40 | heating assembly |
| 41 | atomizing casing |
| 411 | first casing |
| 412 | second casing |
| 42 | heating wire |
| 43 | heating-wire cotton |
| 50 | atomizing chamber |
| 60 | smoking mouthpiece |
| 61 | outer casing |
| 611 | sucking hole |
| 62 | air pipe |
| 70 | contacting pin |

The implementation of aims, the function features and the advantages of the present disclosure are described below in further detail in conjunction with embodiments with reference to the drawings.

DETAILED DESCRIPTION

A clear and complete description as below is provided for the technical scheme in the embodiments of the present disclosure in conjunction with the drawings in the embodiments of the present disclosure. Obviously, the embodiments described hereinafter are simply part embodiments of the present disclosure, but all the embodiments. All other embodiments obtained by the ordinary skill in the art based on the embodiments in the present disclosure without creative work are intended to be included in the scope of protection of the present disclosure.

It should be noted that all directional indications (such as top, bottom, left, right, front, behind . . . ) in the embodiments of the present disclosure are merely to illustrate a relative position relation, a relative motion condition, etc. between each part in a certain state (for example, the state shown in the drawings). If the state changes, the directional indication changes accordingly.

In the present disclosure, unless otherwise specifically stated and defined, terms "connected", "fixed", etc. should be interpreted expansively. For example, "fixed" may be fixed connection, also may be detachable connection, or integration; may be mechanical connection, also may be electrical connection; may be direct connection, also may be indirect connection through an intermediate, and may be internal communication between two elements or interaction of two elements, unless otherwise specifically defined. The ordinary skill in this field can understand the specific implication of the above terms in the present disclosure according to specific conditions.

In addition, if terms "first", "second", etc. appear in the present disclosure, they are merely for the purpose of description, but cannot be understood as the indication or implication of relative importance or as the implicit indication of the number of the designated technical features; therefore, features defined by "first" and "second" may specifically or implicitly include at least one such feature. In addition, technical schemes of each embodiment of the present disclosure may be combined mutually; however, this must be carried out on the basis that the ordinary skill in this field can implement the combination. When the combination of technical schemes has a conflict or cannot be implemented, it should be considered that such combination of technical schemes does not exist and is not in the scope of protection claimed by the present disclosure.

The present disclosure provides an electronic cigarette.

Figure 2:
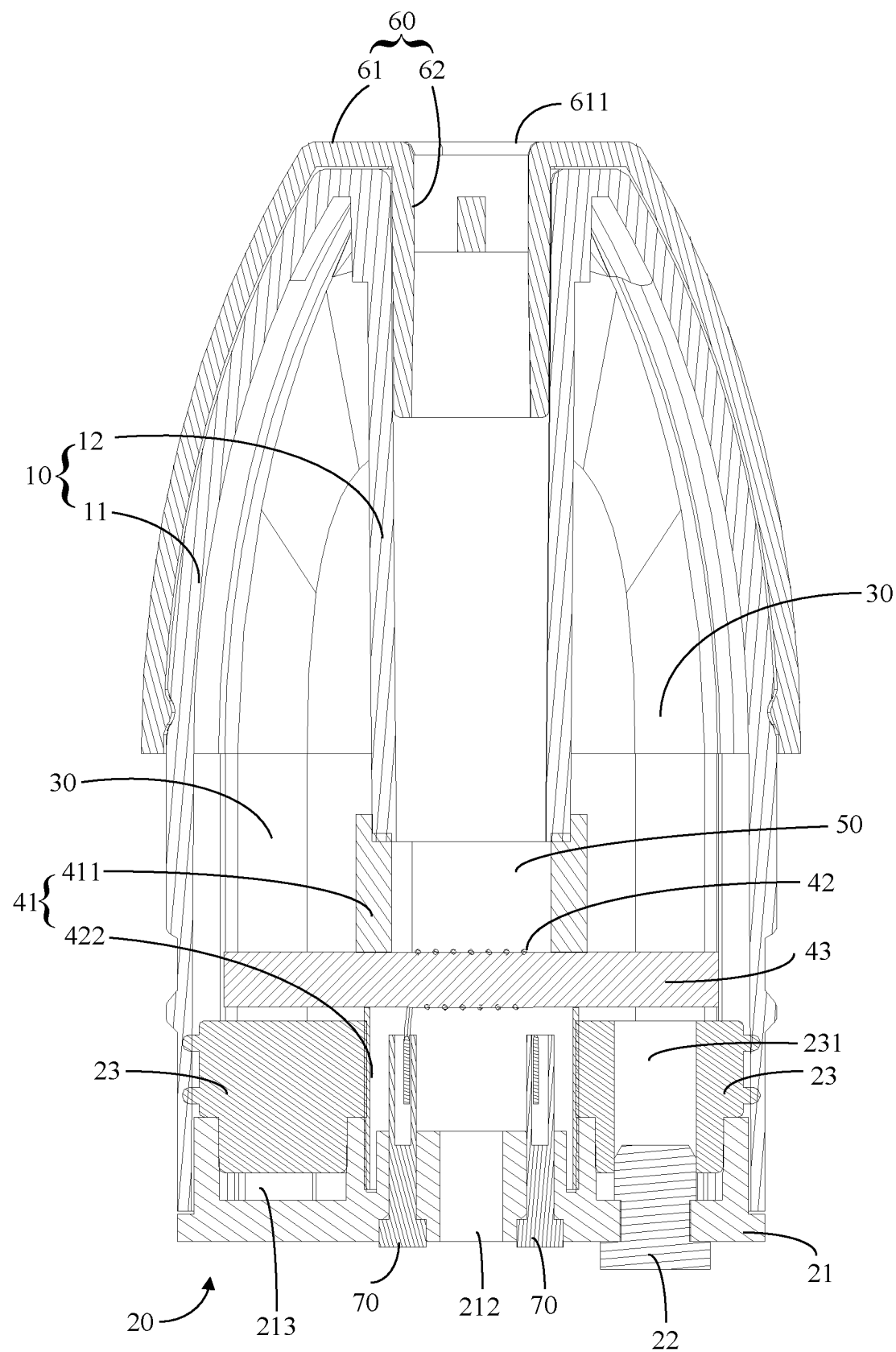
FIG. 2 is a sectional view of the electronic cigarette in FIG. 1.
Figure 3:
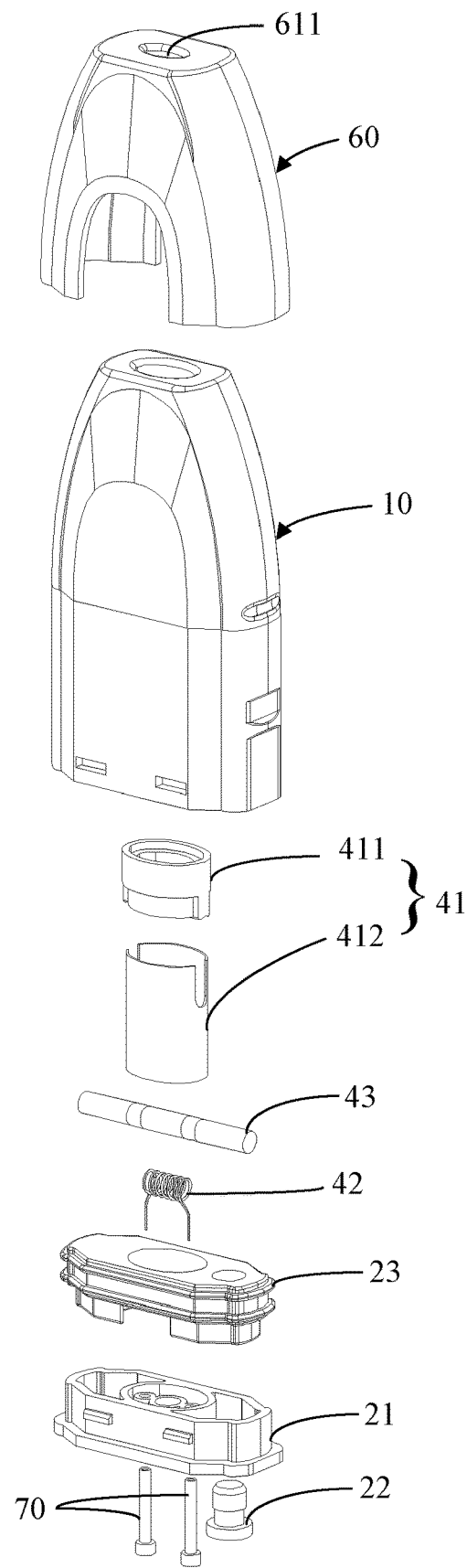
FIG. 3 is an exploded view of the electronic cigarette in FIG. 1.
Figure 4:
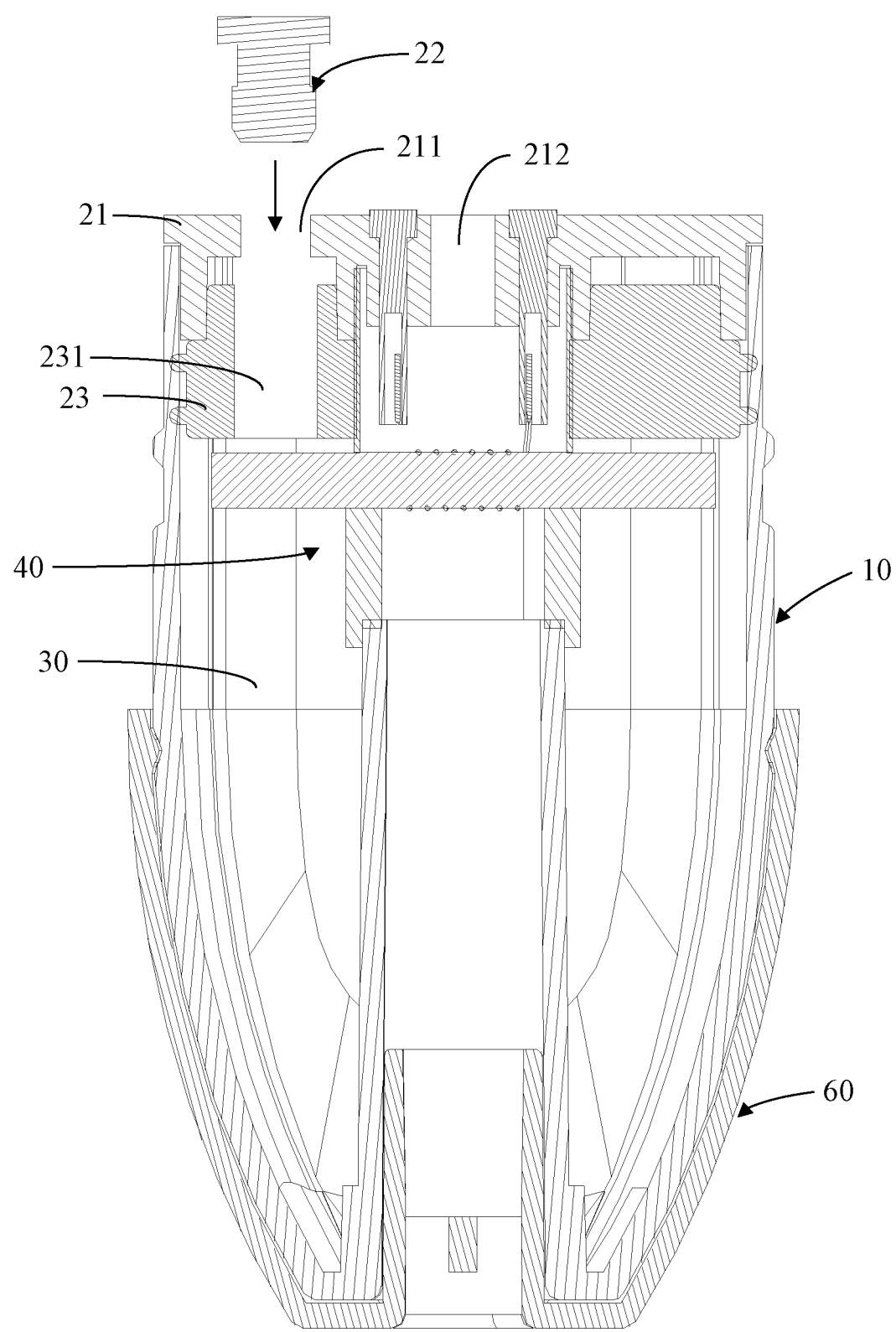
FIG. 4 is a sectional view of the electronic cigarette in FIG. 2 with the sealing element separating from the bottom cover.

Referring to FIGS. 1 to 4, in one embodiment of the present disclosure, the electronic cigarette comprises an upper-cover assembly 10 and a lower-cover assembly 20 interconnected with the upper-cover assembly 10. The upper-cover assembly 10 and lower-cover assembly 20 are cooperated to together form an oil-storing chamber 30. The lower-cover assembly 20 includes a connecting element 23, a bottom cover 21 and a sealing element 22 detachably connected to the bottom cover 21. One end of the connecting element 23 is connected with the bottom cover 21, and the other end of the connecting element 23 is connected with the upper-cover assembly 10. The bottom cover 21 defines an oil-refilling hole 211. The connecting element 23 defines a through hole 231 communicating with both the oil-refilling hole 211 and the oil-storing chamber 30. When the sealing element 22 is connected with the bottom cover 21, the sealing element 22 is passed through the oil-refilling hole 211 and is accommodated in the through hole 231.

The above mentioned sealing element 22 is detachably connected to the bottom cover 21. The sealing element 22 is able to be connected with the bottom cover 21 by a fasten element, such as a screw, a buckle, and so on. It has a simplified structure and is convenient to be used. Furthermore, the sealing element 22 is preferably made of rubber material, such as silica gel stopple and so on. Because of the elastic deformation of the sealing element 22, the oil-refilling hole 211 is sealed tightly. The connecting element 23 herein is preferably made of silica gel material. For one end of the connecting element 23 connecting with the bottom cover 21 and the other end of the connecting element connecting with the upper-cover assembly 10, the structure is simplified and easily assembled. And also the oil-storing chamber 30 formed by the upper-cover assembly 10 in cooperation with the lower-cover assembly 20 has a better sealing performance and is able to proof oil-leakage. Furthermore, the sealing element 22 is passed through the oil-refilling hole 211 and accommodated in the through hole 231 in order to improve sealing appearance of the sealing element 22. The sealing element 22 is not easy to separate from the oil-refilling hole 211 when sealing. And also the sealing element 22 is able to be detached conveniently.

In the present disclosure, one end of the connecting element 23 is connected with the bottom cover 21 and the other end of the connecting element is connected with the upper-cover assembly 10. The bottom cover 21 defines the oil refilling hole 211, and the connecting element 23 defines a through hole 231 communicating with both the oil-refilling hole 211 and the oil-storing chamber 30. When the sealing element 22 is connected with the bottom cover 21, the sealing element 22 extends through the oil refilling hole 211 and is accommodated in the through hole 231. So that the structure of the electronic cigarette is simple, the electronic cigarette can be refilled with oil conveniently and quickly, and further avoid oil-leakage.

Preferably, the electronic cigarette comprises a heating assembly 40 having atomizing chamber 50. The upper-cover assembly 10 comprises a casing 11 and a connecting tube 12 located inside the casing 11. The connecting tube 12 is connected with the heating assembly 40 and communicates with the atomizing chamber 50.

The above mentioned casing 11 and connecting tube 12 are integrated molding structure. The connecting tube 12 and the heating assembly 40 are firmly connected using a fasten element which can be selected from a screw, viscose glue, a buckle and so on, such that the electronic cigarette has a totally simplified structure and be able to be detached conveniently.

Furthermore, the bottom cover 21 defines an air-inlet hole 212. One end of the heating assembly 40 far away from the connecting tube 12 is connected with the bottom cover 21. The atomizing chamber 50 communicates with the air-inlet hole 212. The casing 11, the connecting tube 12, the heating assembly 40 and the bottom cover 21 are cooperated to together form the oil-storing chamber 30. The bottom cover 21 is partially located inside the casing 11. A mounting groove 213 is defined in an end part of bottom cover 21 located inside the casing 11. A portion of the connecting element 23 is accommodated in the mounting groove 213, the other portion of the connecting element 23 is protruded out of the mounting groove 213 to abut against an inner wall of the casing 11.

The bottom cover 21 herein is provided with a mounting position (not labeled) such that the heating assembly 40 is able to be positioned easily and mounted steadily. Because of the mounting groove 213, the connection between the connecting element 23 and bottom cover 21 is steadier, and the connection between the bottom cover 21 and casing 11 is tighter, improving sealing performance of the oil-storing chamber 30.

Preferably, the heating assembly further comprises an atomizing casing 41 defining an atomizing chamber 50, and a heating wire 42 located in the atomizing chamber 50. The atomizing casing 41 defines an oil permeation hole (not labeled) communicating with the atomizing chamber 50 and the oil-storing chamber 30 simultaneously. The electronic cigarette further comprises two contacting pins 70. The bottom cover 21 defines two openings (not labeled) respectively communicating with the atomizing chamber 50. One end of each contacting pin 70 is passed through each opening (not labeled) correspondingly and then connected with the heating wire 42.

The oil in above mentioned oil-storing chamber 30 enter into the atomizing chamber 50 through oil permeation hole (not labeled). Two contacting pin 70 is respectively used for connecting with the positive and negative poles of the battery in order to provide power for the heating wire 42 and ensure steady heating of heating wire 42 for atomizing oil.

Preferably, a quantity of the oil permeation hole (not labeled) is two. The heating assembly 40 further comprises heating-wire cotton 43. The heating-wire cotton 43 is wound by the heating wire 42. Two ends of the heating-wire cotton 43 are passed through two oil permeation holes respectively (not labeled) and locate inside the oil-storing chamber 30.

The above mentioned heating-wire cotton 43 is made of high temperature resistant and high corrosion-resistant materials. The heating wire 42 is spirally wound on the heating-wire cotton 43. For the two ends of the heating-wire cotton 43 extending through two oil permeation holes (not labeled) respectively and locating inside the oil-storing chamber 30, oil inside the oil-storing chamber 30 is able to penetrate in atomizing chamber 50 through the heating-wire cotton 43 so as to atomize oil adequately and improve atomizing effect.

Preferably, the atomizing casing 41 comprises a first casing 411 and a second casing 412 detachably interconnected with the first casing 411. The first casing 411 and second casing 412 are provided with a female fastener (not labeled) and a male fastener (not labeled) respectively. When the first casing 411 is connected with the second casing 412, two oil permeation holes (not labeled) are formed at the contacting part between the female fastener (not labeled) and the male fastener (not labeled).

The first casing 411 herein is preferably made of rubber and the second casing 412 is preferably made of plastic material so that the atomizing casing 41 has a comparatively simplified structure. The first casing 411 and the second casing 412 are detachably connected so that the atomizing casing 41 is able to be mounted and detached conveniently and the heating wire 42 is easy to be replaced. Furthermore, for two oil permeation hole (not labeled) are formed at the contacting part between the female fastener (not labeled) and the male fastener (not labeled), and also for the two ends of the heating-wire cotton 43 locate in the two oil permeation holes (not labeled), the heating-wire cotton 43 is fixed conveniently.

Preferably, the electronic cigarette further comprises a smoking mouthpiece 60 detachably connected to the casing 11. The smoking mouthpiece 60 comprises an air pipe 62. When the smoking mouthpiece 60 is connected with the casing 11, at least a portion of the air pipe 62 is located in the connecting tube 12 and communicated with the connecting tube 12. The smoking mouthpiece 60 herein comprises an outer casing 61 defining a groove and the air pipe 62 located in the groove. When the smoking mouthpiece 60 is connected to the casing 11, the casing 11 is partially located in the groove so that the smoking mouthpiece 60 is connected with the casing 11 more tightly and it is easy and conveniently to be assembled and detached.

The above are preferred embodiments of the present disclosure merely and are not intended to limit the patent scope of the present disclosure. Any equivalent structures made according to the description and the accompanying drawings of the present disclosure without departing from the idea of the present disclosure, or any equivalent structures applied in other relevant technical fields directly or indirectly are intended to be included in the patent protection scope of the present disclosure.

What is to be claimed is:

1. An electronic cigarette, wherein the electronic cigarette comprises an upper-cover assembly and a lower-cover assembly interconnected with the upper-cover assembly, the upper-cover assembly and the lower-cover assembly are cooperated to together form an oil-storing chamber; the lower-cover assembly comprises a connecting element, a bottom cover and a sealing element detachably connected to the bottom cover; one end of the connecting element is connected with the bottom cover, the other end of the connecting element is connected with the upper-cover assembly; the bottom cover defines an oil-refilling hole, the connecting element defines a through hole communicating with both the oil-refilling hole and the oil-storing chamber; when the sealing element is connected with the bottom cover, the sealing element extends through the oil-refilling hole and is accommodated in the through hole.

2. The electronic cigarette according to claim 1, wherein the electronic cigarette comprises a heating assembly having an atomizing chamber; the upper-cover assembly comprises a casing and a connecting tube set inside the casing, the connecting tube is connected with the heating assembly and communicates with the atomizing chamber.

3. The electronic cigarette according to claim 2, wherein the bottom cover defines an air-inlet hole; one end of the heating assembly far away from the connecting tube is connected with the bottom cover, the atomizing chamber communicates with the air-inlet hole; the casing, the connecting tube, the heating assembly and the bottom cover are cooperated to together form the oil-storing chamber.

4. The electronic cigarette according to claim 2, wherein the bottom cover is partially located inside the casing; an mounting groove is defined in an end part of the bottom cover located inside the casing, the connecting element is partially accommodated in the mounting groove, a part of the connecting element exposed from the mounting groove abuts against an inner wall of the casing.

5. The electronic cigarette according to claim 3, wherein the heating assembly further comprises an atomizing casing defining the atomizing chamber and a heating wire located in the atomizing chamber; the atomizing casing defines an oil permeation hole communicating with both the atomizing chamber and the oil-storing chamber.

6. The electronic cigarette according to claim 5, wherein a quantity of the oil permeation hole is two; the heating assembly further comprises heating-wire cotton, the heating-wire cotton is wound by the heating wire, two ends of the heating-wire cotton extend through the two oil permeation holes respectively and locate inside the oil-storing chamber.

7. The electronic cigarette according to claim 6, wherein the atomizing casing comprises a first casing and a second casing detachably interconnected with the first casing; the first casing and the second casing are provided with a female fastener and a male fastener respectively; when the first casing is connected with the second casing, a contacting part between the female fastener and the male fastener defines the two oil-leaking holes.

8. The electronic cigarette according to claim 2, wherein the electronic cigarette further comprises a smoking mouthpiece detachably connected to the casing; the smoking mouthpiece comprises an air pipe; when the smoking mouthpiece is connected to the casing, the air pipe at least partially locates in the connecting tube and communicates with the connecting tube.

9. The electronic cigarette according to claim 5, wherein the electronic cigarette further comprises two contacting pins; the bottom cover defines two openings communicating with the atomizing chamber; one end of each contacting pin extends through a respective opening and is connected with one end of the heating wire.

10. The electronic cigarette according to claim 7, wherein the first casing is made of rubber.

* * * * *